United States Patent
Rome et al.

(10) Patent No.: US 8,772,418 B2
(45) Date of Patent: Jul. 8, 2014

(54) CROSS-LINKER

(75) Inventors: Daniel Rome, Lund (SE); David Persson, Malmo (SE); Erik Lager, Lund (SE); Dane Momcilovic, Lund (SE); Malin Knutsson, Ystad (SE); Jan-Erik Rosenberg, Falkenberg (SE)

(73) Assignee: Nexam Chemical AB, Lund (SE)

( * ) Notice: Subject to any disclaimer, the term of this patent is extended or adjusted under 35 U.S.C. 154(b) by 0 days.

(21) Appl. No.: 13/880,752

(22) PCT Filed: Oct. 21, 2011

(86) PCT No.: PCT/EP2011/068451
§ 371 (c)(1),
(2), (4) Date: Apr. 22, 2013

(87) PCT Pub. No.: WO2012/052550
PCT Pub. Date: Apr. 26, 2012

(65) Prior Publication Data
US 2013/0225769 A1   Aug. 29, 2013

(30) Foreign Application Priority Data

Oct. 22, 2010   (EP) .................................... 10188582

(51) Int. Cl.
*C08G 63/02*   (2006.01)
(52) U.S. Cl.
USPC ........ 525/437; 525/202; 525/328.5; 525/420; 525/421; 528/335; 528/336
(58) Field of Classification Search
USPC ...................... 525/202, 328.5, 420, 421, 437; 528/335, 336
See application file for complete search history.

(56) References Cited

U.S. PATENT DOCUMENTS

| | | | |
|---|---|---|---|
| 5,066,771 A | 11/1991 | Hino et al. | |
| 5,493,002 A | 2/1996 | McGrath et al. | |
| 5,817,744 A * | 10/1998 | Sheppard et al. | 528/353 |
| 6,344,523 B1 | 2/2002 | Hawthorne et al. | |
| 8,492,507 B2 * | 7/2013 | Rosenberg et al. | 528/335 |
| 2011/0190469 A1 * | 8/2011 | Rosenberg et al. | 528/331 |

FOREIGN PATENT DOCUMENTS

| | | |
|---|---|---|
| EP | 1 198 114 A1 | 11/2008 |
| JP | 2010-18056 A | 8/2010 |
| JP | 2010-186055 A | 8/2010 |
| JP | 2010-186134 A | 8/2010 |

OTHER PUBLICATIONS

International Preliminary Report on Patentability for corresponding International Application No. PCT/EP2011/068451 mailed Oct. 5, 2012.
International Search Report for corresponding International Application No. PCT/EP2011/068451 mailed Dec. 12, 2011.
Written Opinion of the International Searching Authority for corresponding International Application No. PCT/EP2011/068451 mailed Dec. 12, 2011.
International Preliminary Report on Patentability for corresponding International Application No. PCT/EP2011/068451 mailed Oct. 10, 2010, 2011.
Extended European Search Report for copending European Application No. 10188582.0 mailed Apr. 20, 2011.
Wolff et al., "3-Substituted Phthalic Acid Derivatives by Sonogashira Coupling Reaction", Synthesis 2007, No. 5, pp. 761-765 and Chemical Abstract.
Hergenrother, "Acetylene-Terminated Imide Oligomers and Polymers Therefrom", Polymer Preprints, American Chemical Society, vol. 21(1), 1980, pp. 81-83.
Dunson, "Synthesis and characterization of Thermosetting Polyimide Oligomers for Microelectronics Packaging", Virginia Polytechnic Institute and State University, Apr. 21, 2000, 264 pages.

* cited by examiner

*Primary Examiner* — Gregory Listvoyb
(74) *Attorney, Agent, or Firm* — Renner, Otto, Boisselle & Sklar, LLP

(57) ABSTRACT

Disclosed are novel cross-linkable end-cappers for oligo- and polyamides. End-capped oligo- and polyamides comprising such an end-capper may be cured at a lower temperature compared to oligo- and polyamides end-capped with PEPA.

6 Claims, 5 Drawing Sheets

CROSS-LINKER

This application is a national phase of International Application No. PCT/EP2011/068451 filed Oct. 21, 2011 and published in the English language, which claims priority to Application No. EP 10188582.0 filed Oct. 22, 2010.

FIELD OF THE INVENTION

The present invention refers to novel cross-linkable endcappers for oligomers and polymers comprising primary amino groups, such as oligo- and polyamides and oligo- and polyimides, and for oligomers and polymers comprising hydroxyl groups, such as oligo- and polyesters, which endcappers comprise carbon-carbon triple bonds. Further, the present invention refers to an end-capped oligomer or polymer. It also relates to an article comprising the oligomer or the polymer, wherein the oligomer or the polymer optionally has been cross-linked by heating.

BACKGROUND

Thermoplastic aliphatic polyamides are often referred to as Nylon. Nylons are typically condensation copolymers formed by reacting a diamine and a dicarboxylic acid or ring-opening polymers formed by polymerization of lactames, such as aminocaproic acid. One of the most common variants is nylon 66, also known as PA 66, which name refers to the fact that the diamine (hexamethylene diamine) and the diacid (adipic acid) each donate 6 carbons to the polymer chain.

Nylon was developed as a synthetic replacement for silk and substituted for it in many different products, such as parachutes, after silk became scarce during World War II. Nylon fibers are today used in many applications, including fabrics, carpets, musical strings, and rope. Solid or reinforced nylon (engineering polymer) is used for mechanical parts such as machine parts, gears, containers, tubes, primary and secondary design elements and other low- to medium-stress components previously cast in metal. Engineering-grade nylon is processed by extrusion, casting, and/or injection molding.

In order to improve the mechanical strength, aromatic polyamides, such as aramid, have been developed. Furthermore, aromatic polyamides are less prone to absorb water than aliphatic polyamides. Absorption of water will affect the mechanical strength negatively. However, the processability of aromatic polyamides is inferior to one of aliphatic polyamides. Further, aromatic polyamides are more brittle and less resistance to chemical solvents compared to aliphatic polyamides.

It would thus be desirable to be able to use aliphatic polyamides in applications wherein aromatic polyamides typically are used.

There have been attempts in the art to improve the mechanical strength of the polyimides, which are related to aromatic polyamides.

U.S. Pat. No. 5,493,002 discloses oligoimides endcapped with PEPA (Phenylethynyl phtalic anhydride). The PEPA endcapped oligoimides are cured, i.e. cross-linked, at about 400° C. Similarly, U.S. Pat. No. 5,066,771 discloses use of EPA (ethynyl phtalic anhydride) as an endcapper for oligoimide. The disclosed EPA endcapped oligoimides was cured, i.e. cross-linked, in a step wise manner including heating at 200° C. for 4 hours, at 250° C. for 2 hours, at 290° C. for 1 hour and lastly at 320° C. for 6 hours.

Further, there have been attempts in the art to improve the mechanical strength of the aromatic polyamides. EP 1 988 114 discloses wholly aromatic polyetheramides endcapped with PEPA. Wholly aromatic polyamides are thermo stable and withstands the heat required to cure the cross-linkable end-capper PEPA.

However, as well known within the art, aliphatic polyamides, such as various types of nylon, are less thermo stable and would degrade at temperatures typically used to cross-link PEPA. Thus, cross-linking of PEPA in polyamides would require catalysis or long term cross-linking at lower temperatures. Accordingly, PEPA has not find use as cross-linkable end-capper for aliphatic polyamides.

As an alternative to PEPA, also ethynyl phtalic anhydride (EPA) has been used as cross-linker in polyimides (cf. Hergenrother, P. M., "Acetylene-terminated Imide Oligomers and Polymers Therefrom", Polymer Preprints, Am. Chem. Soc., Vol. 21 (1), p. 81-83, 1980).

Although polyimides comprising EPA may be cross-linked at a lower temperature, i.e. at about 250° C., it suffers from other drawbacks. The exchange of the phenyl ethynyl group to an ethynyl group implies that other reaction pathways than the desired curing mechanism, such as chain extension, are favored. As a consequence, EPA has not found any wide use as a replacement to PEPA as a low temperature curing end-capper. Further, the manufacture of EPA requires protective group chemistry hampering its commercial potential.

Neither EPA is suitable as end-capper for polyamides. In addition to the drawback mentioned above, cross-linking of EPA will be initiated at temperature below the normal processing temperature, typically 290 to 310° C., of nylon 66, thus limiting its possible use as a cross-linker for nylon 66 end-capped with EPA would, at least to certain extent, cross-link during processing.

Polyamic acids, and their corresponding polyimides, endcapped with PEPA or EPA have been suggested for use in various applications in the art. As an example, JP 2010186134 discloses a photosensitive resin containing an optical base generator (A) and polyamic acid (B), wherein the polyamic acid (B) may have terminal polymerizable group(s). The terminal polymerizable groups are selected from polymerizable groups known in the art, such as anilines or dianhydrides comprising carbon-carbon double or triple bonds. Specifically disclosed examples of polymerizable end-cappers include maleic anhydride, 4-aminocinnamic acid, 4-ethynylaniline, 3a,4,7,7a-tetrahydroisobenzofuran-1,3-dione, 3a,4,7,7a-tetrahydro-4,7-methanoisobenzofuran-1,3-dione, 3a,4,7,7a-tetrahydro-4,7-epoxyisobenzofuran-1,3-dione, EPA and PEPA.

According to Wollf et al (cf. Synthesis, 2007 (5), 761-765) N-phenylphthalimides with carbon substituents in the 3-position, such as (4-(1-octyn-1-yl)-2-phenyl-1H-Isoindole-1,3(2H)-dione, 4-(1-hexyn-1-yl)-2-phenyl-1H-Isoindole-1,3(2H)-dione, and 4-(3,3-dimethyl-1-butyn-1-yl)-2-phenyl-1H-Isoindole-1,3(2H)-dione, are accessible by Sonogashira coupling reaction of the corresponding bromo derivatives. 3-alkyl substituted N-phenylphthalimides may be used as synthetic intermediates for the production of pre-organized hydrogen bonding donors for the synthesis of supramolecular affinity molecules.

U.S. Pat. No. 6,344,523 addresses the disadvantageous of the too high curing temperature of PEPA discussed above and discloses that use of sulfur or organic sulfur derivatives as curing promoters may lower the curing temperature of phenylethynyl terminated imide oligomers. However, the introduction of such promotors suffers from other disadvantages. In particular the curing results in chain extension rather than cross-linking as two ethynyl groups react along with one sulfur radical ultimately forming a thiophene structure.

Thus, there is need within the art for an alternative cross-linking monomer, overcoming the above-mentioned deficiencies, to be used as cross-linking monomer for aliphatic polyamides, such as PA66.

SUMMARY

Consequently, the present invention seeks to mitigate, alleviate, eliminate or circumvent one or more of the above-identified deficiencies in the art and disadvantages singly or in any combination by providing a compound according to formula (I) or (II)

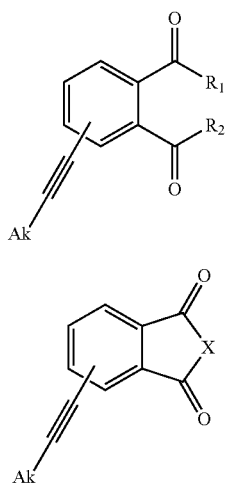

wherein

R1 and R2 are independently selected from the group consisting of OH, halo, OC1-C8 alkyl, NH2, NHC1-8 alkyl, N(C1-8 alkyl)$_2$, wherein said alkyl may be the same or different, OC(O)C1-8 alkyl, OC0-1 alkylenephenyl, and NHC0-1 alkylenephenyl;

"Ak" is a C1-10 alkyl or C0-1 alkylene cyclohexyl; and

"X" is selected from the group consisting of "O" (oxygen), NH, NC1 alkylenephenyl, and NC1-8 alkyl; or a compound according to formula (II), wherein "Ak" is a C1-10 alkyl or C0-1 alkylene cyclohexyl; and "X" is NHphenyl; with the proviso that said compound not is (4-(1-octyn-1-yl)-2-phenyl-1H-Isoindole-1,3(2H)-dione, 4-(1-hexyn-1-yl)-2-phenyl-1H-Isoindole-1,3(2H)-dione, or 4-(3,3-dimethyl-1-butyn-1-yl)-2-phenyl-1H-Isoindole-1,3 (2H)-dione Especially, in compounds according to formula (I) and R1 and R2 may be independently selected from the group consisting of OH, halo, OC1-C8 alkyl. Further, in compounds according to formula (II) "X" may be "O" (oxygen). Furthermore, "Ak" may be methyl in compounds according to formula (I) or (II). The alkyn residue, i.e. AK-≡-, may connected to the 4- or 5-position of the benzene residue of said compound according to formula (I) or (II)

Thus, one typical compound according to formula (II) is 5-(prop-1-yn-1-yl)isobenzofuran-1,3-dione.

Another aspect of the invention relates to compounds which may be obtained by use of a compound according to formula (I) or (II). Such compounds may thus be compounds comprising at least one residue of a compound according to formula (I) or (II), wherein said residue is a residue according to formula (III) or (IV),

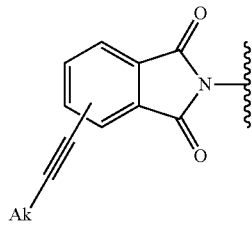

wherein the waved line indicates the point of attachment to the rest of the compound;

"Ak" is a residue in accordance with any one of the claim 1 or 3;

"A" is "O" (oxygen) or NH; and

R3 is OH, OC1-C8 alkyl, NH2, NHC1-8 alkyl, N(C1-8 alkyl)$_2$, wherein said alkyl may be the same or different, OC0-1 alkylenephenyl, NHC0-1 alkylenephenyl,

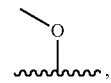

wherein the waved line indicates the point of attachment to the rest of the compound, or

wherein the waved line indicates the point of attachment to the rest of the compound, with the proviso that said compound according to formula (III) not is (4-(1-octyn-1-yl)-2-phenyl-1H-Isoindole-1,3(2H)-dione, 4-(1-hexyn-1-yl)-2-phenyl-1H-Isoindole-1,3(2H)-dione, or 4-(3,3-dimethyl-1-butyn-1-yl)-2-phenyl-1H-Isoindole-1,3(2H)-dione.

Compounds comprising a residue according to formula (III) or (IV) may be an oligo- or polyamide, such as an aliphatic oligo- or polyamide, comprising at least one residue, such as at least 10, 25, or 50 residues, of a monomer selected from the group consisting of hexamethylene diamine, pentamethylene diamine, 2,2,4-trimethyl-hexamethylene diamine, 2,4,4-trimethyl-hexamethylene diamine, 1,4-diaminobutane, 1,2-diaminobenzene, 1,3-diaminobenzene, and 1,4-diaminobenzene and at least one residue, such as at least 10, 25, or 50 residues, of a monomer selected from the group consisting of oxalic acid, maloic acid, adipic acid, sebacic acid, isophthalic acid, terephthalic acid and 2,5-furandicarboxylic acid; or an oligo- or polyamide comprising at least one residue of a monomer selected from the group consisting of caprolactame, 11-aminoundecanoic acid, 12-aminodecanoic acid, and aminocaproic acid. If the oligo- or polyamide comprises a residue according to formula (IV), then "A" may be NH.

Further, compounds comprising a residue according to formula (III) may be an oligo- or a polyimide comprising at least one residue, such as 2 to 40 residues, of pyromellitic dianhydride or of a dianhydride according to the general formula (XV),

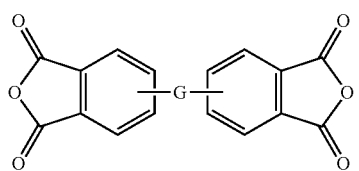

(XV)

wherein "G" represents a direct bond or a di-valent group selected from the group consisting of a carbonyl group, a methylene group, a sulfone group, a sulfide group, an ether group, an —C(O)-phenylene-C(O)— group, an isopropylidene group, a hexafluoroisopropylidene group, a 3-oxyphenoxy group, a 4-oxyphenoxy group, a 4'-oxy-4-biphenoxy group, and a 4-[1-(4-oxyphenyl)-1-methylethyl]phenoxy group; and wherein "G" may be connected to the 4- or 5-position and the 4'- or the 5'-position, respectively, in the isobenzofuran-1,3-dione residues; and at least one residue, such as 2 to 40 residues, of 1,4-diaminobenzene, 1,3-diaminobenzene, or a diamine according to the general formula (XVI)

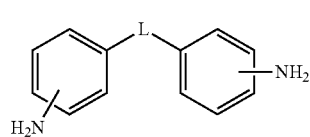

(XVI)

wherein the amino groups may be connected to any substitutable carbon atom in the benzene residues, i.e. to the 2-, 3- or 4-position, and the 2', 3', or 4'-position, respectively; and "L" is a direct bond or a moiety selected from the group consisting of —O—, —S—, —SO$_2$—, —C(O)—, —C(CH$_3$)$_2$—, —C(CF$_3$)$_2$—, —CH$_2$—, 3-oxyphenoxy group, 4-oxyphenoxy group, 4'-oxy-4-biphenoxy group, and 4-[1-(4-oxyphenyl)-1-methylethyl]phenoxy group.

Furthermore, compounds comprising a residue according to formula (IV), wherein "A" is "O" oxygen, may be an oligo- or polyester.

Additionally, the reactivity of compounds according to formula (I) or (II) may be altered by reaction with compounds comprising a first primary amino group. Such compounds with altered reactivity may, in addition to a residue according to formula (III), comprise at least one group selected from the group consisting of NH2, OH, COR4, wherein R4 is OH, halo, OC1-C8 alkyl, OC(O)C1-8 alkyl, OC0-1 alkylenephenyl, vinyl, and COH.

Another aspect of the invention relates to a compound according to formula XX

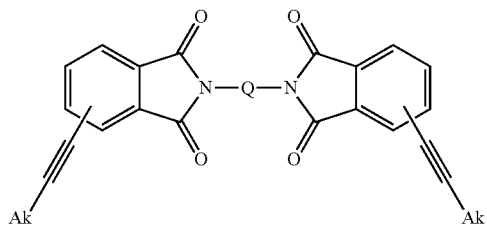

(XX)

wherein "Ak" is C1-10 alkyl, such as methyl, or C0-1 alkylene cyclohexyl; and

Q is selected from the group consisting of C2-12 alkylene, phenylene, C1-4 alkylene-phenylene-C1-4 alkylene, or C0-4 alkylene-cyclohexandiyl-C0-4 alkylene.

Another aspect of the invention relates to a composition comprising an oligomer or a polymer comprising residue according to formula (III) or (IV). Such an oligomer or a polymer may further comprise an additional polymer, and/or at least one filler, reinforcement, pigment, external flame retardant, stabilizer, and/or plasticizer. The amount oligomer or a polymer comprising residue according to formula (III) or (IV) in such a composition may be at least 10 wt %.

Another aspect of the invention relates to a method of producing a compound according to formula (I) or (II). Such a method comprises the step(s) of:

reacting a chlorophthalic anhydride, a bromophthalic anhydride, or an iodophthalic anhydride, such as 4-bromophtalic anhydride, or a compound according to formula (V) or (VI)

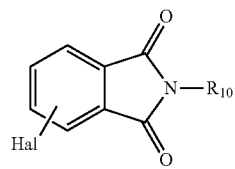

(V)

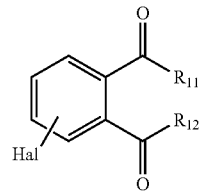

(VI)

wherein
"Hal" is chloro, bromo, or iodo, such as bromo;
R10 is H, C1-8 alkyl or C0-1 alkylenephenyl; and
R11 and R12 are independently selected from the group consisting of OC1-8 alkyl, OC0-1 alkylenephenyl, NH2, NHC1-8 alkyl, N(C1-8 alkyl)$_2$, wherein said alkyl may be the same or different, and NHC0-1 alkylenephenyl;
with a compound according to formula (VII),

(VII)

wherein
"Ak" is a residue in accordance with any one of the claim 1 or 3, to obtain a compound according to formula (I) or (II); and
optionally purifying the obtained compound according to formula (I) or (II) by use of chromatography or recrystallization.

Another aspect of the invention relates to a method of introducing a compound according to formula (II),

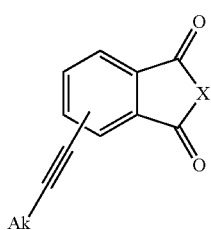

wherein "Ak" is a C1-10 alkyl or C0-1 alkylene cyclohexyl; and
"X" is "O" (oxygen);
into an oligo- or polyamide, comprising the steps of:
melting the oligo- or polyamide to be reacted with the compound according to formula (II);
mixing the oligo- or polyamide with the compound according to formula (II); and
allowing the oligo- or polyamide to react with the compound according to formula (II).

Further advantageous features of the invention are defined in the dependent claims. In addition, advantageous features of the invention are elaborated in embodiments disclosed herein.

DETAILED SUMMARY OF PREFERRED EMBODIMENTS

Definitions

In the context of the present application and invention, the following definitions apply:

As used herein, "halo" or "halogen" refers to fluoro, chloro, bromo, and iodo.

As used herein, "alkyl" used alone or as a suffix or prefix, is intended to include both branched and straight chain saturated aliphatic hydrocarbon groups having from 1 to 12 carbon atoms or if a specified number of carbon atoms is provided then that specific number is intended. For example "C1-6 alkyl" denotes alkyl having 1, 2, 3, 4, 5 or 6 carbon atoms. When the specific number denoting the alkyl-group is the integer 0 (zero), a hydrogen-atom is intended as the substituent at the position of the alkyl-group. For example, "N(C0 alkyl)$_2$" is equivalent to "NH2" (amino).

As used herein, "alkylenyl" or "alkylene" used alone or as a suffix or prefix, is intended to include straight chain saturated aliphatic hydrocarbon groups having from 1 to 12 carbon atoms or if a specified number of carbon atoms is provided then that specific number is intended. For example "C1-6 alkylenyl" "C1-6 alkylene" denotes alkylenyl or alkylene having 1, 2, 3, 4, 5 or 6 carbon atoms. When the specific number denoting the alkylenyl or alkylene-group is the integer 0 (zero), a bond is intended to link the groups onto which the alkylenyl or alkylene-group is substituted. For example, "NH(CO alkylene)NH$_2$" is equivalent to "NHNH$_2$" (hydrazino). As used herein, the groups linked by an alkylene or alkylenyl-group are intended to be attached to the first and to the last carbon of the alkylene or alkylenyl-group. In the case of methylene, the first and the last carbon is the same. For example, "H$_2$N(C2 alkylene)NH$_2$", "H$_2$N(C3 alkylene)NH$_2$", "N(C4 alkylene)", "N(C5 alkylene)" and "N(C2 alkylene)$_2$NH" is equivalent to 1,2-diamino ethane, 1,3-diamino propane, pyrrolidinyl, piperidinyl and piperazinyl, respectively.

Examples of alkyl include, but are not limited to, methyl, ethyl, n-propyl, propyl, n-butyl, i-butyl, sec-butyl, t-butyl, pentyl, and hexyl.

Examples of alkylene or alkylenyl include, but are not limited to, methylene, ethylene, propylene, and butylene.

As used herein, the term "aryl" refers to a ring structure, comprising at least one aromatic ring, made up of from 5 to 14 carbon atoms. Ring structures containing 5, 6, 7 and 8 carbon atoms would be single-ring aromatic groups, for example phenyl. Ring structures containing 8, 9, 10, 11, 12, 13, or 14 carbon atoms would be polycyclic, for example naphthyl. The aromatic ring may be substituted at one or more ring positions. The term "aryl" also includes polycyclic ring systems having two or more cyclic rings in which two or more carbons are common to two adjoining rings (the rings are "fused rings") wherein at least one of the rings is aromatic, for example, the other cyclic rings may be cycloalkyls, cycloalkenyls, cycloalkynyls, and/or aryls.

The terms ortho, meta and para apply to 1,2-, 1,3- and 1,4-disubstituted benzenes, respectively. For example, the names 1,2-dimethylbenzene and ortho-dimethylbenzene are synonymous.

As used herein, the term "substitutable" refers to an atom to which a hydrogen may be covalently attached, and to which another substituent may be present instead of the hydrogen. A non-limiting example of substitutable atoms include the carbon-atoms of pyridine. The nitrogen-atom of pyridine is not substitutable according to this definition.

Embodiments

It has unexpectedly been revealed that polyamides comprising a residue of a compound according to formula (I) or (II), e.g. compounds endcapped with such a compound,

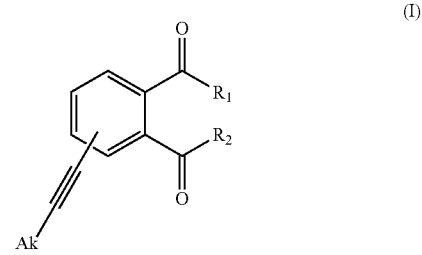

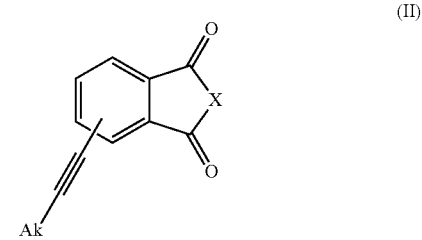

wherein R1 and R2 are independently selected from the group consisting of OH, halo, OC1-C8 alkyl, such as methoxy and ethoxy, NH2, NHC1-8 alkyl, N(C1-8 alkyl)$_2$, wherein said alkyl may be the same or different, OC(O)C1-8 alkyl, OC0-1 alkylenephenyl, and NHC0-1 alkylenephenyl; Ak is C1-10 alkyl, such as methyl, or C0-1 alkylene cyclohexyl; and "X" is selected from the group consisting of "O" (oxygen), NH, NC1 alkylenephenyl, and N—C1-8 alkyl; or
polyamides comprising a residue of a compound according to formula (II), wherein "Ak" is a C1-10 alkyl or C0-1 alkylene cyclohexyl; and "X" is NHphenyl; with the proviso that the compound not is (4-(1-octyn-1-yl)-2-phenyl-1H-Isoindole-1,3(2H)-dione, 4-(1-hexyn-1-yl)-2-phenyl-1H-Isoindole-1,3(2H)-dione, or 4-(3,3-dimethyl-1-butyn-1-yl)-2-phenyl-1H-Isoindole-1,3(2H)-dione; may be cross-linked at a slightly lower temperature than polyamides comprising a residue of PEPA, i.e. at about 310° C.

This temperature is high enough to allow normal processing of an aliphatic oligo- or polyamide, such as PA66, comprising a residue of a compound according to formula (I) or (II), without initiating curing, i.e. cross-linking, to any substantial extent. However, an aliphatic oligo- or polyamide comprising a residue of a compound according to formula (I) or (II) may, in contrast to an oligo- or polyamide comprising a residue of PEPA, be cured, i.e. cross-linked, without any significant thermo degradation of the oligo- or polyamide.

Thus, an embodiment of the present invention relates to a compound according to formula (I) or (II) as disclosed herein.

In compounds according to formula (I), R1 and R2 may further, independently of each other, be selected from the group consisting of OH, halo, such as chloro, and OC1-C8 alkyl, such as methoxy and ethoxy. In compounds according to formula (II) "X" may further be "O" (oxygen).

According to an embodiment, "Ak" in compounds according to formula (I) or (II) may be methyl, ethyl, propyl, isopropyl, n-butyl, tert-butyl, n-pentyl, neopentyl. Preferably, "Ak" is methyl in compounds according to formula (I) or (II).

In compounds according to formula (I) or (II), the alkyn residue, i.e. may be connected to any of the substitutable carbon atoms of the benzene residue. It is preferred if the alkyn residue is attached to the 4- or 5-position of the benzene residue, wherein position 1 and 2 are the ones being fused with the furan-1,3-dione moiety.

Accordingly, an embodiment of the present invention relates to a compound according to formula (II), wherein the compound is

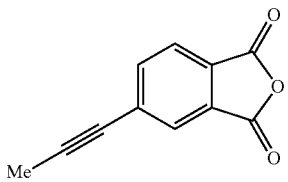 [SMILES: CC#Cc1ccc2c(c1)C(=O)OC2=O]

(5-(prop-1-yn-1-yl)isobenzofuran-1,3-dione; also denoted MEPA (methylethynyl phthalic anhydride) herein).

Compounds according to formula (I) or (II) may be used to obtain compounds comprising residues of compounds according to formula (I) or (II). Thus, an embodiment relates to a compound comprising at least one residue of a compound according to formula (I) or (II), wherein said residue is a residue according to formula (III) or (IV),

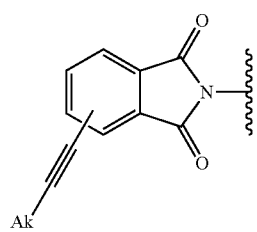

(III)

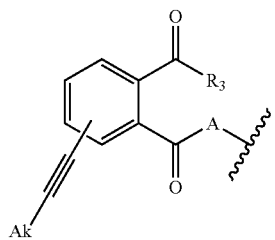

(IV)

wherein the waved line indicates the point of attachment to the rest of the compound;

"Ak" is C1-10 alkyl, such as methyl, or C0-1 alkylene cyclohexyl, i.e. "Ak" in formula (III) or (IV) is a residue corresponding to "Ak" in formula (I) or (II);

"A" is "O" (oxygen) or NH; and

R3 is OH, OC1-C8 alkyl, NH2, NHC1-8 alkyl, N(C1-8 alkyl)$_2$, wherein said alkyl may be the same or different, OC0-1 alkylenephenyl, NHC0-1 alkylenephenyl,

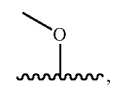 [SMILES: *OC]

wherein the waved line indicates the point of attachment to the rest of the compound, or

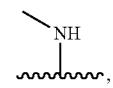

wherein the waved line indicates the point of attachment to the rest of the compound; with the proviso that said compound comprising a residue according to formula (III) not is (4-(1-octyn-1-yl)-2-phenyl-1H-Isoindole-1,3(2H)-dione, 4-(1-hexyn-1-yl)-2-phenyl-1H-Isoindole-1,3(2H)-dione, or 4-(3,3-dimethyl-1-butyn-1-yl)-2-phenyl-1H-Isoindole-1,3 (2H)-dione.

Compounds according to formula (I) or (II) are suitable as end-cappers for oligomers and polymers comprising functional group(s) which may react with carboxylic anhydrides, such as compounds according to formula (II), or carboxylic acids or derivatives thereof, such as compounds according to formula (I). Such functional group(s) may be selected from group consisting of primary amino groups, hydroxy groups and epoxy groups.

Thus, another embodiment relates to an oligo- or polyamide, an oligo- or polyimide, an oligo- or polyester, or an epoxy resin comprising at least one residue of a compound according to formula (I) or (II) as disclosed herein. Similarly, an embodiment relates to an oligo- or polyamide, an oligo- or polyimide, a oligo- or polyester, or an epoxy resin obtainable by reacting compound according to formula (I) or (II), as disclosed herein, with an oligo- or polyamide, an oligo- or polyimide, a oligo- or polyester, or an epoxy resin. Such an end-capped oligo- or polyamide, oligo- or polyimide, oligo- or polyester or epoxy resin may accordingly comprise a residue according to formula (III) or (IV),

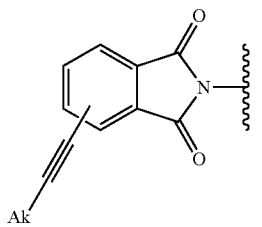
(III)

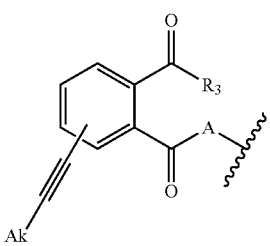
(IV)

wherein the waved line indicates the point of attachment to the rest of the oligomer or the oligomer or the polymer; "Ak" is, as disclosed herein above, a C1-10 alkyl, such as methyl, or C0-1 alkylene cyclohexyl; "A" is "O" (oxygen) or NH; and R3 is OH, OC1-C8 alkyl, NH2, NHC1-8 alkyl, N(C1-8 alkyl)$_2$, wherein said alkyl may be the same or different, OC0-1 alkylenephenyl, NHC$_{0-1}$ alkylenephenyl,

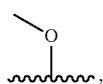

wherein the waved line indicates the point of attachment to the rest of the compound, or

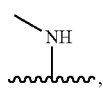

wherein the waved line indicates the point of attachment to the rest of the oligomer or polymer.

Compounds comprising a residue according to formula (IV), wherein, R3 is

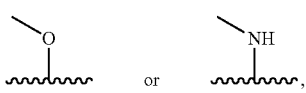

may be seen as the result of chain extension, i.e. compounds according to formula (I) or (II) may be used to link at least two oligo- or polymer chains together, thereby positioning the triple bond pendant and not at the end of the oligomer or polymer chain.

Primary amino groups reacting with a compound according to formula (I) or (II) will initially give rise to compound comprising a residue according to formula (IV), wherein "A" is NH. To improve the stability, the compound comprising a residue according to formula (IV) may then be imidized, such as by dehydration eliminating water, to form compound comprising a residue according to formula (III).

Hydroxy groups reacting with a compound according to formula (I) or (II) or epoxy groups reacting with a compound according to formula (I), given that at least one of R1 and R2 is hydroxyl, or (II), given that "X" is "O" (oxygen), will give rise to compound comprising a residue according to formula (IV), wherein "A" is "O" (oxygen).

Common examples of oligo- and polyamides, which may be end-capped or chain elongated with compounds according to formula (I) or (II), comprises Nylon 6, 66, 46, 69, 610, 612, 11, 12, 6T, 6I, 6DT, or mixtures thereof. Preferably, the oligo- or polyamide is a high amino oligo- or polyamide. According to an embodiment, high amino oligo- or polyamides are oligo- or polyamides wherein the statistically percentage of end groups being an amino group exceeds 50%, such as oligo- or polyamides wherein the statistically percentage of end groups being an amino group exceeds 75%.

According to an embodiment, the oligo- and polyamide, to be end-capped or chain elongated with compounds according to formula (I) or (II), may be an aliphatic oligo- or polyamide, such as PA6, having a melting point of 220° C., PA66, having a melting point of 260° C., and PA46, having a melting point of 295° C. Preferably, the aliphatic oligo- or polyamide may be PA66. Furthermore, mixture of more than one type of oligo- and polyamide may be used. As known to the skilled artisan, the melting points of blends of polymers may be adjusted by varying the content of polymers present in the blend as well the type of polymers.

Further, the oligo- and polyamide, which may be end-capped or chain elongated with compounds according to formula (I) or (II) may be a semiaromatic oligo- or polyamide, such as PA6I.

Such a cross-linkable oligo- or polyamide as disclosed herein above may comprise at least one residue, such as at least 10, 25, or 50 residues, of a monomer typically used to obtain oligo- or polyamides. Monomers typically used to obtain oligo- or polyamide as condensation co-polymers comprises diamines such as, hexamethylene diamine, pentamethylene diamine, 2,2,4-trimethyl-hexamethylene diamine, 2,4,4-trimethyl-hexamethylene diamine, 1,4-diaminobutane, 1,2-diaminobenzene, 1,3-diaminobenzene, and 1,4-diaminobenzene, and di-carboxylic acids such as, oxalic acid, maloic acid, adipic acid, sebacic acid, isophthalic acid, terephthalic acid and 2,5-furandicarboxylic acid. Monomers typically used to obtain oligo- or polyamide as ring-opening polymers comprises lactames such as, caprolactam. Also linear aminoacids, such as 11-aminoundecanoic acid, 12-aminodecanoic acid, and aminocaproic acid, may be used to obtain oligo- and polyamides.

Oligo- or polyamides comprising a cross-linkable end-capper according to formula (III) or (IV), may be aliphatic oligo- or polyamides. Monomers typically used to obtain such aliphatic oligo- or polyamide as condensation co-polymers comprises aliphatic diamines such as, hexamethylene diamine, pentamethylene diamine, 2,2,4-trimethyl-hexamethylene diamine, 2,4,4-trimethyl-hexamethylene diamine, 1,4-diaminobutane, and aliphatic di-carboxylic acids such as, oxalic acid, maloic acid, adipic acid, sebacic acid. Monomers typically used to obtain aliphatic oligo- or polyamide as ring-opening polymers comprises lactames such as, caprolactam. Also linear aminoacids, such as 11-aminoundecanoic acid, 12-aminodecanoic acid, and aminocaproic acid, may be used to obtain aliphatic oligo- or polyamide.

As known to the skilled artisan, polyamides are hard to dissolve. Thus, although possible, it may be disadvantageous to introduce a compound according to formula (I) or (II) via a chemical reaction in solution. Further, modification of polymers in solution is general avoided as far as possible as it introduces additional steps into a production process dissolution and evaporation.

One option to introduce a compound according to formula (I) or (II) into oligo- and polyamide is to have them present as an additional constituent during the polymerization. However, although compounds according to formula (I) or (II) may act as chain extenders, the degree of polymerization would anyhow most likely be negatively affected. Further, the very long polymerization reaction times tend to decrease the yield of the cross-linker incorporated due to degradation.

However, it has unexpectedly been found that compounds according to formula (I) or (II), and especially compounds according to formula (II), wherein "X" is "O" (oxygen), may be introduced into polyamides by melt modification, i.e. be mixing compounds according to formula (I) or (II) into melted polyamides. Although, melt modification of polyamide to blend fillers, pigments, external flame retardant, stabilizers, plasticizer into the polyamide is known within the art, it is unexpected that compounds according to formula (I) or (II) may be effectively introduced into polyamides without degrading the polymer or the compound it self.

As an example, 5-(prop-1-yn-1-yl)isobenzofuran-1,3-dione may be incorporated into a polyamide, such as PA66, by using a single or twin screw mixer, e.g. compounder, or a extruder. The mixer is typically operated at the normal processing temperature for the specific polyamide, e.g. 290° C. to 300° C. for a standard polyamide 66. Preferably, the screw-length/diameter ratio should be large enough to attain sufficient yield of the reaction, e.g. 3 min at 290° C. At lower processing temperatures the residence time may has to be increased in order to attain sufficient yield. As an example, the screw-length/diameter ratio may thus be at least 15, such as between 15 and 40. Alternatively a melt mixer can be used, just increasing the mixing time until incorporation is complete.

An embodiment thus relates to method of introducing a cross-linkable aromatic carboxylic acid anhydride comprising a carbon-carbon triple bond, such as a compound according to formula (II), wherein "X" is "O" (oxygen), such as MEPA, into oligo- or polyamides, such as PA66. Such a method typically comprises the steps of:

melting the oligo- or polyamide to be reacted with the aromatic carboxylic acid anhydride;
mixing the oligo- or polyamide with the aromatic carboxylic acid anhydride; and
allowing the polyamide to react with the aromatic carboxylic acid anhydride.

The polyamide may be melted prior, during, or subsequently to being mixed with the aromatic carboxylic acid anhydride. As indicated above, the melting and mixing may be performed a single or twin screw mixer, e.g. compounder extruder. The obtained cross-linkable polyamide may comprise a residue according to formula (III) or (IV) as disclosed herein above.

Examples of a cross-linkable aromatic carboxylic acid anhydride comprising a carbon-carbon triple bond, which may be introduced by melt mixing, are not limited to compounds according to formula (II), wherein "X" is "O" (oxygen). Further examples of cross-linkable aromatic carboxylic acid anhydride comprising a carbon-carbon triple bond include EPA, PEPA, 5-(3-phenylprop-2-ynoyl)isobenzofuran-1,3-dione and related derivatives.

According to an embodiment, examples of cross-linkable aromatic carboxylic acid anhydride comprising a carbon-carbon triple bond, which may be introduced by melt mixing are compounds according to formula XXV

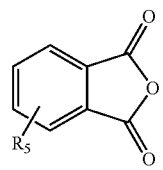

(XXV)

wherein

R5 is —C1-5 alkyl, such as -≡-Me, -≡-H, -≡-Ph, wherein the phenyl group may be substituted with one or several substituents independently selected from the group consisting of fluoro, nitro, phenyl, phenoxy, trifluoromethyl, alkyl, SO3H, or SO3$^-$. In compounds according to formula (XXV), R1 may be connected to any of the substitutable carbon atoms of the benzene residue. It is preferred if the respective alkyn residue is attached to the 4- or 5-position of the respective benzene residue, wherein position 1 and 2 are the ones being fused with the respective furan-1,3-dione moiety.

Furthermore, not only oligo- or polyamides may be end-capped via melt mixing with a cross-linkable aromatic carboxylic acid anhydride comprising a carbon-carbon triple bond. Also other polymers, comprising functional group(s) which may react with carboxylic anhydrides, which polymers may be melted at a lower temperature than the temperature at which cross-linking is initiated, may be end-capped via melt mixing. Such functional group(s) may be selected from group consisting of primary amino groups, hydroxy groups and epoxy groups. As an example, also epoxides and polyesters may be end-capped via melt mixing.

Common examples of oligo- and polyesters, which may end-capped or chain extended with compounds according to formula (I) or (II), comprises poly(ethylene terephthalate) (PET), poly(ethylene naphthalate) (PEN), poly(propylene terephthalate) (PPT) and poly(butylene terephthalate) (PBT).

Such a cross-linkable oligo- or polyester as disclosed herein above may comprise at least one residue, such as at least 5, 10, or 20 residues of a monomer typically used to obtain oligo- or polyesters. Monomers typically used to obtain oligo- or polyesters comprises terephthalic acid anhydride and aliphatic diols, such as ethylene glycol, 2,3-butandediol and 1,3-propanediol.

Such a cross-linkable oligo- or polyimide as disclosed herein above may comprise at least one residue, such as from 2 to 40 or 4 to 20 residues of a monomer typically used to obtain oligo- or polyimides. Monomers typically used to obtain oligo- or polyimide as condensation co-polymers comprises aromatic carboxylic dianhydrides, such as pyromellitic dianhydride, 4,4'-oxydiphtalic anhydride, 2,2-bis-[4-(3,4-dicarboxyphenoxy)phenyl]-propane dianhydride, 3,3',4,4'-benzophenonetetracarboxylic acid dianhydride, 3,3',4,4'-tetracarboxybiphenyl dianhydride, 4,4',5,5'-sulfonyldiphthalic anhydride, and 5,5'-(perfluoropropane-2,2-diyl)bis(isobenzofuran-1,3-dione), and aromatic diamines, such as 4,4'-oxydianiline, 1,4-diaminobenzene, 1,3-diaminobenzene, 1,3-bis-(4-aminophenoxy)benzene, 1,3-bis-(3-aminophenoxy)benzene, methylenedianiline, and 3,4'-oxydianiline.

According to an embodiment, the aromatic dianhydride used to obtain the oligo- or polyimide may be pyromellitic dianhydride or a dianhydride according to the general formula (XV),

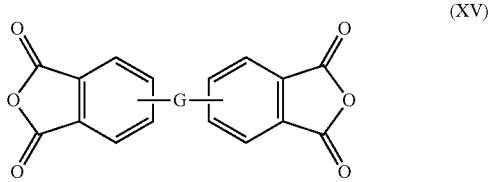

(XV)

wherein "G" represents a direct bond or a di-valent group selected from the group consisting of a carbonyl group, a methylene group, a sulfone group, a sulfide group, an ether group, an —C(O)-phenylene-C(O)— group, an isopropylidene group, a hexafluoroisopropylidene group, a 3-oxyphenoxy group, a 4-oxyphenoxy group, a 4'-oxy-4-biphenoxy group, and a 4-[1-(4-oxyphenyl)-1-methylethyl]phenoxy group; and wherein "G" may be connected to the 4- or 5-position and the 4'- or the 5'-position, respectively, in the isobenzofuran-1,3-dione residues.

According to an embodiment, the aromatic diamine used to obtain the oligo- or polyimide may be 1,4-diaminobenzene, 1,3-diaminobenzene, or a diamine according to the general formula (XVI)

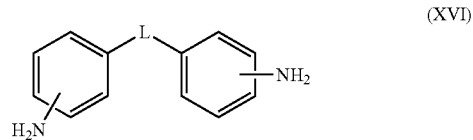

(XVI)

wherein the amino groups may be connected to any substitutable carbon atom in the benzene residues, i.e. to the 2-, 3- or 4-position, and the 2', 3', or 4'-position, respectively; and "L" is a direct bond or a moiety selected from the group consisting of —O—, —S—, —SO$_2$—, —C(O)—, —C(CH$_3$)$_2$—, —C(CF$_3$)$_2$—, —CH$_2$—, 3-oxyphenoxy group, 4-oxyphenoxy group, 4'-oxy-4-biphenoxy group, and 4-[1-(4-oxyphenyl)-1-methylethyl]phenoxy group. Preferably, the amino groups are connected to the 3- or 4-position of the respective benzene residue. Symmetric di-amines, eg. 3,3'- and 4,4'-substited di-amines according to general formula (XVI), as well as asymmetric di-amines, eg. 3,4'-, or 4,3'- substited di-amines according to general formula (XVI), are equally possible.

As well known in the art, asymmetric aromatic diamines and dianhydrides may be used to prepare polyimides with a bent and rotationally hindered structure resulting in high Tg but also in improved processability and high melt fluidity along with and solubility of the resin in organic solvent. Symmetric aromatic dianhydrides as well asymmetric aromatic dianhydrides are equally possible.

An oligomer or a polymer comprising a residue according to formula (III) or (IV), may, according to an embodiment, have a number average molecular weight of about 1,000 to 40,000, such as from about 10,000 to 30,000. The number average molecular weight may be determined with size exclusion chromatography (SEC), such as gel permeation chromatography (GPC).

Another embodiment relates to composition comprising an oligomer or polymer comprising a residue according to formula (III) or (IV). Further, the composition may comprise more than one type of oligomer or polymer comprising a residue according to formula (III) or (IV), such as at least two different types of polyamides. The composition may further comprise at least one additional polymer, such as at least one additional oligo- or polyamide, at least one additional oligo- or polyimide, or at least one additional oligo- or polyester, and/or at least one filler, reinforcement, pigment, external flame retardant, stabilizer, plasticizer and/or any other additive known in the art. The oligomer or polymer comprising a residue according to formula (III) or (IV) is preferably present in an amount corresponding to at least 10 wt %, such as at least 25, 40, 60, or 80 wt % of the composition. Furthermore, such a composition may also comprise a compound according to formula (I) or (II).

Another embodiment relates to an article comprising an oligomer or polymer comprising a residue according to formula (III) or (IV). Optionally, the oligomer or the polymer in the article has been cross-linked by heating it. Typically examples of articles comprising such oligomers or polymers include specialty organic fibers, such as meta- and para-Aramids, Polybenzimidazole (PBI), Polyethylene, Polyimide, Polyamideimide (PAI), Liquid Crystal Polymer Fibers.

Another embodiment relates to an article comprising an oligomer or polymer comprising a residue according to formula (III) or (IV). Optionally, the oligomer or the polymer in the article has been cross-linked by heating it.

Typically examples of articles comprising an oligo- or polyimide comprising a residue according to formula (III) or (IV), include flexible films for electronics, wire isolation, wire coatings, wire enamels, ink, and load-bearing structural components.

Typically examples of articles comprising an oligo- or polyamide comprising a residue according to formula (III) or (IV), include synthetic fibers, automotive parts, industrial machinery, electronics, films, wires, cables, tubing, pipes and stock shapes.

Typically examples of articles comprising a oligo- or polyester comprising a residue according to formula (III) or (IV), include synthetic fibers and containers, such bottles for beverages.

Similar to PEPA and EPA, also compounds according to formula (I) or (II), as well as compounds comprising a residue of such a compound, may cross-linked by heating them. Without being bound to any theory, it is believed that, upon heating of mixtures of compounds comprising ethynyl moieties, these moieties will eventually start to react. Reaction of two ethynyl moieties of separate molecules will provide a chain extended product, while reaction of three ethynyl moieties of separate molecules is thought to provide a benzene moiety with three "arms". Subsequently, two or three ethynyl moieties present on such "arms" may react to form a cross-linked product. Chain extension, but especially cross-linking, will improve the properties of an oligo- or polymer comprising ethynyl moieties, as has been shown in the art. Heat initiated chain extension, but especially cross-linking, of oligo- or polymers comprising ethynyl moieties is often referred to as curing.

The curing of compounds, such as oligo- or polyamide, comprising a residue according to formula (III) or (IV), and compositions or articles comprising an oligo- or polyamide comprising a residue according to formula (III) or (IV), may be accomplished by heating.

Such heating may be performed in an isothermal staging process. As an example, such an isothermal staging process may start by heating the material to be cured to 250° C. to 350° C., such as at about 280° C., for some time, typically 1 to 2 hours. However, also less time, such as less than 1 hour, or less than 30 minutes, may be used. Further, also longer times, such as up to 10 hours may be used. Subsequently, the temperature may be increased in steps. Each step may correspond to an increase of the temperature of 5° C. to 25° C.

Further, each step may have a duration of 30 minutes to 10 hours, such as 1 to 2 hours. The last step may be curing at a temperature of 300 to 350° C., such as at about 350° C.

While temperatures exceeding 350° C. should be avoided for longer periods of time, curing at temperatures may be tolerated for short periods of time, such as less than 1 minute. Especially, polymer films may be cured at temperatures exceeding 350° C. for short periods of time.

In an isothermal staging process the duration of each isothermal step may decrease as the temperature increases. By employing an isothermal staging process curing may be promoted over degradation, especially if the time of each step is decreased as the temperature is increased. A further example of an isothermal staging process, is a process starting at 200° C. in which the temperature is increased by 25° C. every hour until 350° C. is reached.

The curing may also be accomplished by isothermal heating at a temperature of 250° C. to 350° C., such as 280° C. to 330° C. The time of the isothermal heating may be 1 to 24 hours, such as 5 to 15 hours.

The curing may also be a heating process with continuously increasing temperature. Preferably, the heating rate is slow initially but gradually increased as the temperature increases.

A curing cycle for oligo- or polyamide comprising a residue according to formula (III) or (IV) may in addition to a curing stage also encompass a pre-curing stage and/or a post-curing stage.

As well known within the art, the preparation of oligo- and polyimides are preferably performed in, but not limited to, aprotic solvents, such as dimethylacetamide, dimethylformaide or N-Methylpyrrolidone. Typically, oligo- and polyimides are prepared at a dry weight of the monomers corresponding to about 10 to 40 wt %.

In the preparation of oligo- and polyimides, the monomers are mixed at ambient or at slightly elevated temperature, typically from about 25° C. to 50° C., to obtain an oligo- or a polyamic acid as intermediate. Then, the oligo- or polyamic acid intermediate is imidized at a much higher temperature, such as about 180° C., by dehydration eliminating water.

Analogously to PEPA and EPA, compounds according to formula (I) or (II), such as MEPA, may be, as readily understood by the skilled artesian, incorporated in different ways into oligo- and polyimides.

As an example, compounds according to formula (I) or (II) may be co-polymerized into the polyimide by addition initially or at an early stage to a reaction mixture comprising di-amine and di-anhydride monomers to be polymerized. Examples of aromatic di-amines and di-anhydrides have been given herein above.

As the formation of oligo- and polyimides involves formation of oligo- or polyamic acid intermediates, oligo- or polyamic acid intermediates end-capped with a compound according to formula (I) or (II) as well as oligo- or polyimide end-capped with a compound according to formula (I) or (II), may be isolated.

Compounds of formula (I) or (II) may also be reacted with an amino terminated oligo- or polyamic acid or an amino terminated oligo- or polyimide, respectively, after their preparation.

The dissertation thesis "*Synthesis and characterization of thermosetting polyimide oligomers for microelectronics packaging*" by Debra Lynn Dunson, Virginia Polytechnic Institute and State University, from 2000, provides information relating to the preparation of PEPA end-capped oligo- and polyimides. Similar procedures may be employed to prepare oligo- and polyimides comprising residues of compounds according to formula (I) or (II) as disclosed herein. Thus, the dissertation thesis "*Synthesis and characterization of thermosetting polyimide oligomers for microelectronics packaging*" by Debra Lynn Dunson, Virginia Polytechnic Institute and State University, from 2000 is incorporated herein by reference.

As well known to the skilled artisan, various polyamides and polyesters may be obtained as disclosed herein below.

In preparing Nylon 66, Adipic acid (derived from cyclohexane) and hexa-methylene-diamine (most commonly derived from butadiene or acrylonitrile) are prereacted to form nylon salt that is particularly well suited to purification. Subsequently, the purified nylon salt is heated and, as water is removed, the polycondensation proceeds, current production units operate both continuously and by batch procedures.

In preparing Nylon 6, Caprolactam (derived from cyclohexane or phenol) is reacted in the molten state with controlled amounts of water to obtain intermediate epsilon-aminocaproic acid, which readily condenses to the corresponding polyamide 6 as water is removed under controlled conditions of temperature and pressure.

Nylon 46 resin is produced by reacting 1,4-diaminobutane with adipic acid. 1,4-Diaminobutane is derived by reacting acrylonitrile with hydrogen cyanide and subsequent reduction of the intermediate.

Nylon 69 resins are produced (via an intermediate) from hexamethylene diamine and azelaic acid. Azelaic acid is typically derived from tallow (via oleic acid).

Nylon 610 resins are produced (via an intermediate) from hexamethylene diamine and sebacic acid. Sebacic acid is usually derived from castor oil.

Nylon 612 resins are produced (via an intermediate) from hexa-methylene-diamine and dodecanedioic acid (DDDA), which is most often derived (via cyclododecane) from butadiene.

Copolymer 6/12 resins are prepared from DDDA, caprolactam, hexa methylene diamine, adipic acid and/or other materials.

Nylon 11 resins are obtained from the self-condensation of 11-amino-undecanoic acid, which is typically derived from castor oil.

Nylon 12 resins are obtained from laurolactam in much the same manner in which nylon 6 is obtained from caprolactam. Laurolactam is usually derived (via cyclododecane) from butadiene.

PPA (polyphthalamide) is a copolymer made from terephthalic, isophthalic, and adipic acids and hexa-methylene-diamine.

As disclosed above, compounds according to formula (I) or (II) may be reacted with an amino terminated or the amino end groups of an oligo- or polyamide after their preparation.

Polybutylene terephthalate (PBT) resin is produced by the polycondensation of approximately equal molar proportions of 1,4-butanediol and dimethyl terephthalate (DMT). The first step in the reaction is transesterification, in which 1,4-butanediol replaces the methyl groups in the DMT molecule to form bis-(4-hydroxybutyl)-terephthalate (BHBT) and methyl alcohol, as shown below. The liberated methyl alcohol is removed from the reaction system to drive the exchange to near completion. PBT is produced by polycondensation of BHBT usually in the presence of a catalyst (commonly based on titanium) under reduced pressure at 240-260° C. As polycondensation occurs, 1,4-butanediol is produced and is removed from the polycondensation reaction as a vapor.

Virgin Polyethylene terephthalate (PET) polymer is produced by polycondensation of ethylene glycol with either dimethyl terephthalate (DMT) or terephthalic acid (TPA) via intermediate bis-(2-hydroxyethyl)-terephthalate (BHET).

Compounds of formula (I) or (II) may be reacted with hydroxy terminated or the hydroxy end groups of an oligo- or polyester after their preparation.

The reactivity of compounds according to formula (I) or (II) may be altered by reaction with compounds comprising a first primary amino group. By use of compounds, which, in addition to a first primary amino group, also comprises a functional group selected from the group consisting of —NH2, —OH, —COR4, wherein R4 is OH, halo, OC1-C8 alkyl, OC(O)C1-8 alkyl, OC0-1 alkylenephenyl, vinyl, and COH, compounds according to formula (I) or (II) may be used to obtain cross-linkers for oligomers and polymers having terminal hydroxyl or carboxy groups, such as polycarbonates and polyesters, for oligomers and polymers made by polymerization of monomers comprising carbon-carbon double bonds, eg. styrene, acrylic acid, methacrylic acid, ethene, and propene, oligomer and for polymers made by polymerization of phenols and aldehydes, etc.

As readily understood by the skilled artisan, it may be necessary to protect one of the functional groups of the compounds comprising a first primary amino group upon reacting compounds compound according to formula (I) or (II) with such compounds.

Further, in order to enhance the reactivity, R4 may, as readily understood by the skilled artisan, be converted into an activated carboxy group before being incorporated into an oligomer or a polymer having terminal hydroxyl group(s).

Examples of aromatic compounds comprising a first primary amino group, and which are suitable to alter the reactivity of compounds according to formula (I) or (II), comprises aminophenols or a minoresorcinols, O-acetylated aminophenols or O-acetylated a minoresorcinols, aminobenzoic or aminophthalic acids or esters.

Examples of aliphatic compounds for altering the reactivity of compounds according to formula (I) or (II), comprises aminoalcohols, such as ethanolamine, di-ethanolamine, and 2-amino-2-(hydroxymethyl)-1,3-propandiol, amino acids, such as glycine, alanine, beta-alanine, 4-amino butanoic acid, 6-amino-hexanoic acid, 11-aminoundecanoic acid, 12-aminodecanoic acid, and aminocaproic acid, 5-amino-4-oxopentanoic acid, and glycyl-glycine.

An embodiment relates to a compound selected from the group consisting of

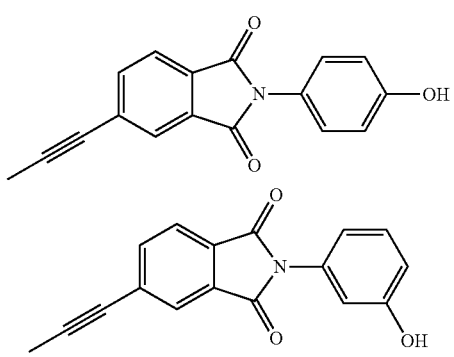

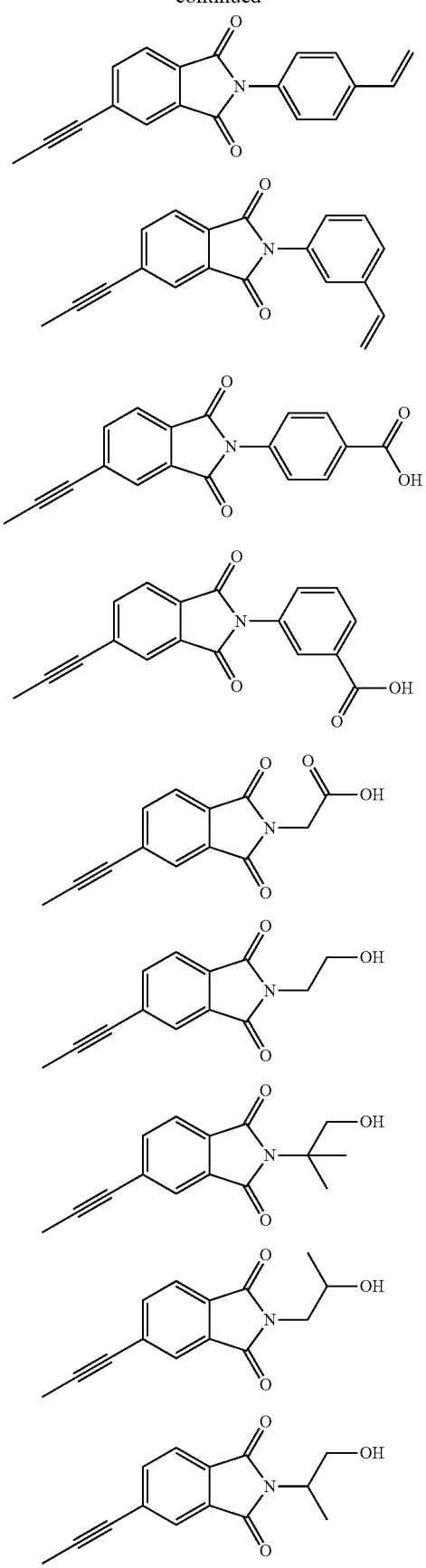

-continued

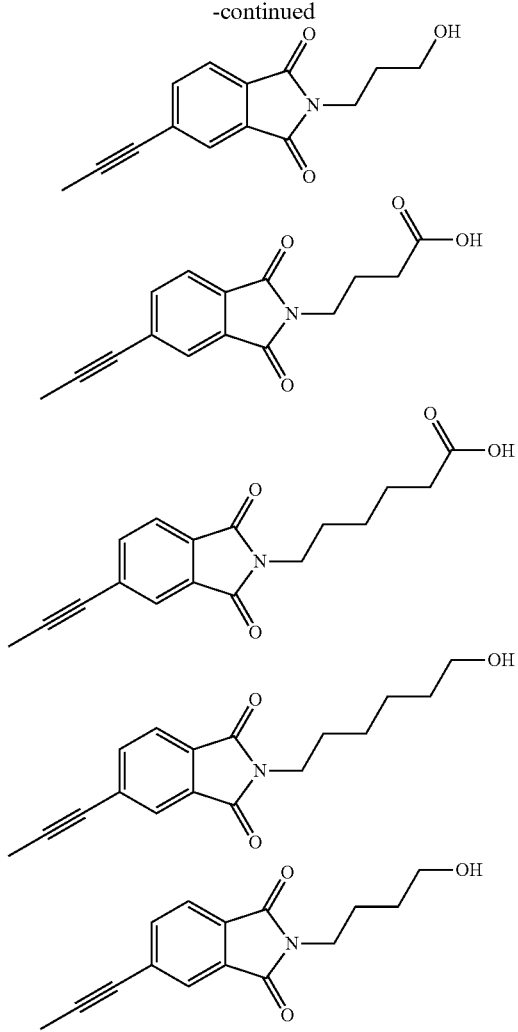

Further, compounds according to formula (I) or (II) may be used to obtain compounds comprising two carbon-carbon triple bonds. Such compounds may used to enhance the degree of cross-linking. Examples of such compounds are

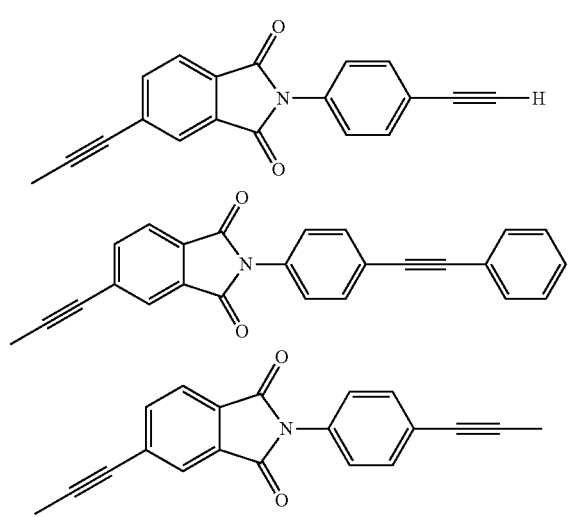

-continued

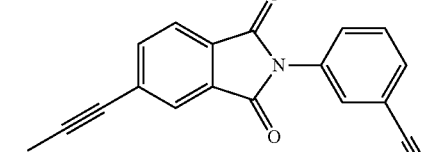

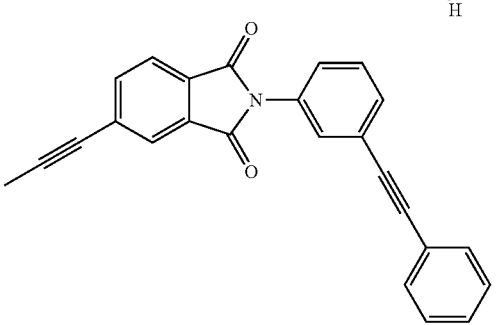

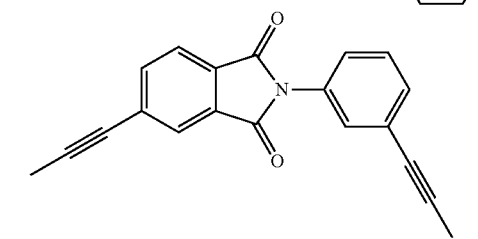

Typically, such compounds comprising two carbon-carbon triple bonds are mixed into composition comprising an oligomer or a polymer comprising a residue according to formula (III) or (IV). When used in such a composition they may act as reactive solvent and/or plasticizer to improve processability without compromising the amount of cross-linkers. Such mixing may be performed by melt mixing. As described herein, compounds according to formula (II), wherein "X" is "O" (oxygen), may be incorporated into oligo- and polyamides by meltmixing. Before, during, or subsequent to incorporating compounds according to formula (II), wherein "X" is "O" (oxygen), into oligo- and polyamides, by melt mixing, the oligo- and polyamides may be melt mixed with a compound comprising two carbon-carbon triple bonds.

Further, additional examples of compounds comprising two carbon-carbon triple bonds and which may used to enhance the degree of cross-linking, are compounds which may be obtained be reacting two equivalents of a compound according to formula (I) or (II) with one equivalents of a diamine, such as phenylene diamine or hexamethylene amine.

An embodiment relates to a compound according to formula XX (XX)

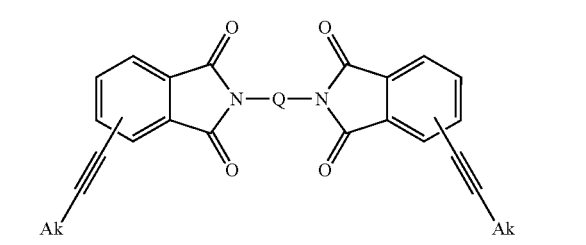

wherein "Ak" is C1-10 alkyl, such as methyl, or C0-1 alkylene cyclohexyl; and

Q is selected from the group consisting of C2-12 alkylene, phenylene, C1-4 alkylene-phenylene-C1-4 alkylene, or C0-4 alkylene-cyclohexandiyl-C0-4 alkylene. Preferably, "Ak" is C1-3 alkyl, such as being methyl. Furthermore, Q is preferably tetramethylene, hexamethylene, or phenylene. In a compound according to formula (XX), the alkyn residue, i.e. AK-≡-, may be connected to any of the substitutable carbon atoms of the respective benzene residue. It is preferred if the respective alkyn residue is attached to the 4- or 5-position of the respective benzene residue, wherein position 1 and 2 are the ones being fused with the respective furan-1,3-dione moiety.

According to an embodiment, the compound according to formula (II) is 2,2'-(hexane-1,6-diyl)bis(5-(prop-1-yn-1-yl) isoindoline-1,3-dione).

A further embodiment relates to a compound according to formula (XX) wherein
"Ak" is C1-10 alkyl, such as methyl, or C0-1 alkylene cyclohexyl; and
"Q" is a radical selected from the group consisting of:

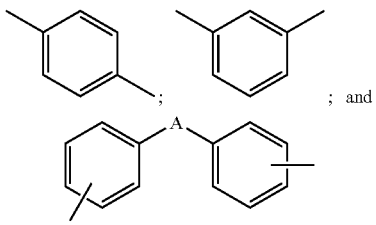

wherein "A" is a direct bond or a moiety selected from the group consisting of —O—, —S—, —SO$_2$—, —C(O)—, —C(CH3)2—, —C(CF3)2—, —CH2-, 3-oxyphenoxy group, 4-oxyphenoxy group, 4'-oxy-4-biphenoxy group, and 4-[1-(4-oxyphenyl)-1-methylethyl]phenoxy group.

Furthermore, such compounds, comprising two carbon-carbon triple bonds and which may be used to enhance the degree of cross-linking, and which have been described herein above, may be present in a composition, comprising an oligomer or polymer comprising a residue according to formula (III) or (IV) herein.

A further embodiment relates to a method of producing a compound according to formula (I) or (II) as disclosed herein. Such a method comprises the step of:
reacting a chlorophthalic anhydride, a bromophthalic anhydride, or an iodophthalic anhydride, such as 4-bromophtalic anhydride, a derivative thereof, or a compound according to formula (V) or (VI)

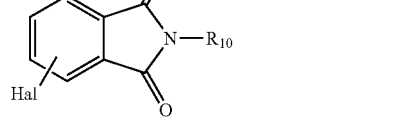

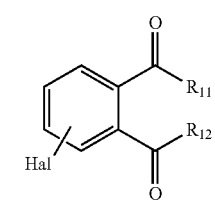

wherein "Hal" is chloro, bromo, or iodo, such as bromo;
R10 is H, C1-8 alkyl or C1 alkylenephenyl; and R11 and R12 are independently selected from the group consisting of OC1-8 alkyl, OC0-1 alkylenephenyl, NH2, NHC1-8 alkyl, N(C1-8 alkyl)$_2$, wherein said alkyl may be the same or different, and NHC0-1 alkylenephenyl; with a compound according to formula (VII)

wherein "Ak" is a C1-10 alkyl, such as methyl, or C0-1 alkylene cyclohexyl, to obtain a compound according to formula (I) or (II); and
optionally purifying the obtained compound according to formula (I) or (II). In a preferred embodiment, 4-bromophtalic anhydride is reacted with propyne to obtain MEPA.

The reaction between the chlorophthalic anhydride, the bromophthalic anhydride, or the iodophthalic anhydride, and the compound according to formula (V) may typically be a palladium catalyzed coupling reaction, such as a Sonagashira coupling. According to one embodiment, the reaction may thus be performed in the presence of a compound comprising palladium, such as Bis(triphenylphosphine)palladiumchloride, and a compound comprising cupper, such as CuI. A phosphine, such as tri-phenylphsophine, may be also added to the reaction mixture.

Further, the crude product may be purified via standard techniques, such as chromatography or re-crystallization. Chromatography may typically be normal phase chromatography on silica. Re-crystallization may be performed in solvents such as, aromatic hydrocarbons, optionally with the addition of carboxylic acids, such as formic or acetic acid.

According to an embodiment, compounds according to formula (II), such as compound obtained via the method above, may be purified by normal phase chromatography on silica using an organic solvent or a mixture of organic solvents, such as heptane/ethyl acetate (80/20).

According to another embodiment, compounds according to formula (II), such as compound obtained via the method above, may be purified by re-crystallization in solvents, such as aromatic hydrocarbons, eg. toluene or xylene. In such re-crystallization, the yield may be increased by addition of carboxylic acids, such as formic or acetic acid.

Although the present invention has been described above with reference to specific embodiments, it is not intended to be limited to the specific form set forth herein. Rather, the invention is limited only by the accompanying claims and, other embodiments than the specific above are equally possible within the scope of these appended claims, e.g. different than those described above.

In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous.

In addition, singular references do not exclude a plurality. The terms "a", "an", "first", "second" etc do not preclude a plurality.

Experimental

Figure 1:
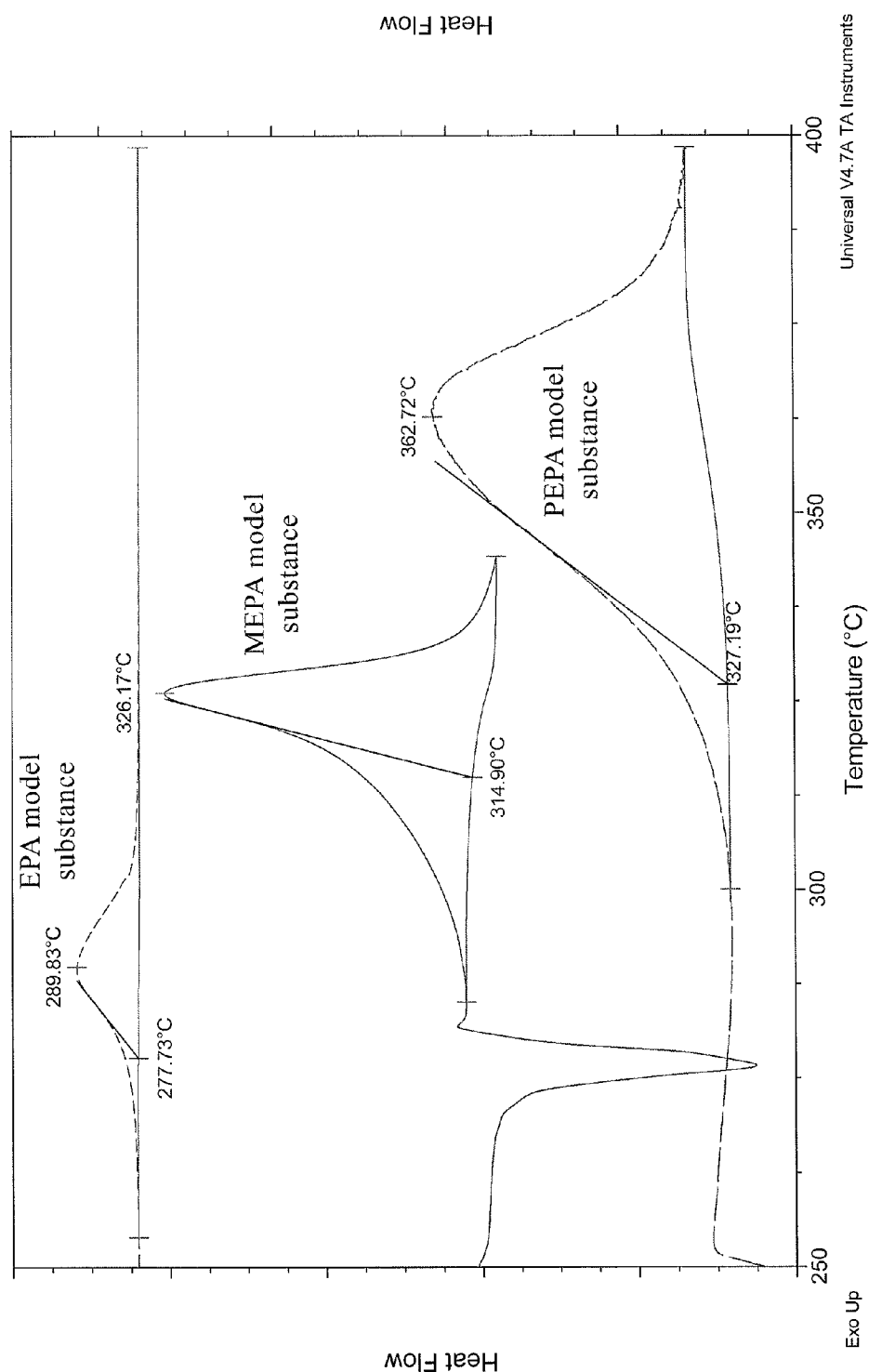
FIG. 1 depicts a DSC scan of EPA, MEPA and PEPA, respectively, imidized with phenylenediamine.

The following examples are mere examples and should by no mean be interpreted to limit the scope of the invention. Rather, the invention is limited only by the accompanying claims.

ABBREVIATIONS

PEPA Phenylethynyl phtalic anhydride
EPA Ethynyl phtalic anhydride
MEPA 5-(prop-1-yn-1-yl)isobenzofuran-1,3-dione
PD-MEPA 2,2'-(1,3-phenylene)bis(5-(prop-1-yn-1-yl)isoindoline-1,3-dione)
HD-MEPA 2,2'-(hexane-1,6-diyl)bis(5-(prop-1-yn-1-yl)isoindoline-1,3-dione)

5-(prop-1-yn-1-yl)isobenzofuran-1,3-dione (MEPA)

Bromophtalic anhydride (50.0 g, 0.22 mol), triethylamine (33.8 mL, 0.24 mol) and toluene (220 mL) were mixed in a glass reactor over nitrogen (g) atmosphere at room temperature. Bis(triphenylphosphine)palladiumchloride (0.77 g, 0.001 mol), CuI (0.42 g, 0.002 mol) and triphenylphosphine (0.87 g, 0.003 mol) were added and the temperature was raised to 50° C. Propyne (18.0 g, 0.45 mol) was slowly added through a gas inlet during 3 hours. The reaction mixture was filtered through a glass filter funnel and the solution was concentrated to dryness to give crude solid product (40.1 g, 98%). The product was re-crystallized from toluene to give a light yellow solid (24.7 g, 60%).

Melting Point of MEPA
109-110° C. (as determined with DSC)
H-NMR of MEPA
$^1$H NMR (400 MHz, d-DMSO): δ=2.15 (s, 3H), 7.94-8.05 (m, 3H).
HPLC-MS of Methanolyzed MEPA Approximately 3 mg MEPA was dissolved in anhydrous MeOH at a concentration of 1 mg/mL. The solution was sonicated for 30 minutes. 200 μL MEPA solution were mixed with 300 μL MeOH:HOAc (100:0.1), (A), and 300 μL it H2O:MeOH:HOAc (95:5:0.1), (B). The resulting mixture was injected onto the LC/UV/MS (inj. vol. 2 μL) Separation was performed on a Dr. Maisch Reprosphere C18 AQ column (100×2.1 mm; dp 3 μm). The mobile phase was comprised of 40% A and 60% B and the flow rate was 0.100 mL/min. UV detection was performed at 254 nm and the MS operated in positive ion scanning mode m/z 190-260. A peak with $R_t$ 15.6 min, corresponding to methyl ethynyl phthalic acid (MH$^+$205 and MNa$^+$227), and two peaks with $R_t$ 26.7 and 29.4, respectively, corresponding to the two region isomers of methyl ethynyl phthalic acid mono-methyl ester (MH$^+$—H$_2$O 201 and MNa$^+$241), were seen.

Phenylenediamine end-capped with MEPA (PD-MEPA; phenylene)bis(5-(prop-1-yn-1-yl)isoindoline-1,3-dione))

MEPA (1.8 g, 9.7 mmol), phenylenediamine (0.48 g, 4.4 mmol) and acetic acid (12 mL) were mixed and heated to 40° C. for 10 minutes. The reaction was then heated to reflux for 24 hours and allowed to cool down to room temperature. The reaction mixture was filtered through a Buchner funnel and the precipitate was washed two times with Methanol (5 mL). The product was dried in a vacuum oven at 50° C. at 50 mbar over night to give a grey product (1.6 g, 82%).

Melting Point of Phenylenediamine End-Capped with MEPA

The melting point was found to be 280° C. as determined by DSC Q2000

H-NMR of Phenylenediamine End-Capped with MEPA
$^1$H-NMR (d-DMSO) δ: 2.15 ppm (6H, s); 7.53-7.58 (3H, m); 7.67-7.73 (1H, m); 7.87-7.97 (6H, m).

The obtained MEPA end-capped phenylenediamine, as well as corresponding phenylenediamine end-capped with EPA and PEPA, respectively, were analyzed by differential scanning calorimetry (DSC) using a TA instrument DSC Q2000. The heating profile employed was: Heat: 35° C.=>400° C. (10°/min).

As seen from FIG. 1, the onset of curing for phenylenediamine end-capped with MEPA was above 300° C., but below the onset of curing for phenylenediamine end-capped with PEPA. Thus, the results in FIG. 1 confirm that polyamides end-capped with MEPA may be cross-linked at higher temperatures compared to the corresponding system end-capped with EPA, thus allowing normal processing of end-capped PA 66 without initiating cross-linking.

PA66 End-Capped with MEPA

PA66 was end-capped with MEPA (1.5 wt %) and PEPA (1.5 wt %), respectively, by melt mixing using a Brabender Plasticoder. The barrel/mixter temperature was set to 290° C. and MEPA was added into the melted polymer. The mixture was mixed for 2 minutes.

The melt viscosity as a function of temperature for the PA66 end-capped with MEPA was determined using a TA Instrument Ares G2 and compared to the melt viscosity of neat PA66. Further, Tan δ as a function of temperature for PA66 end-capped with MEPA was compared with the one for neat PA66.

Figure 2:
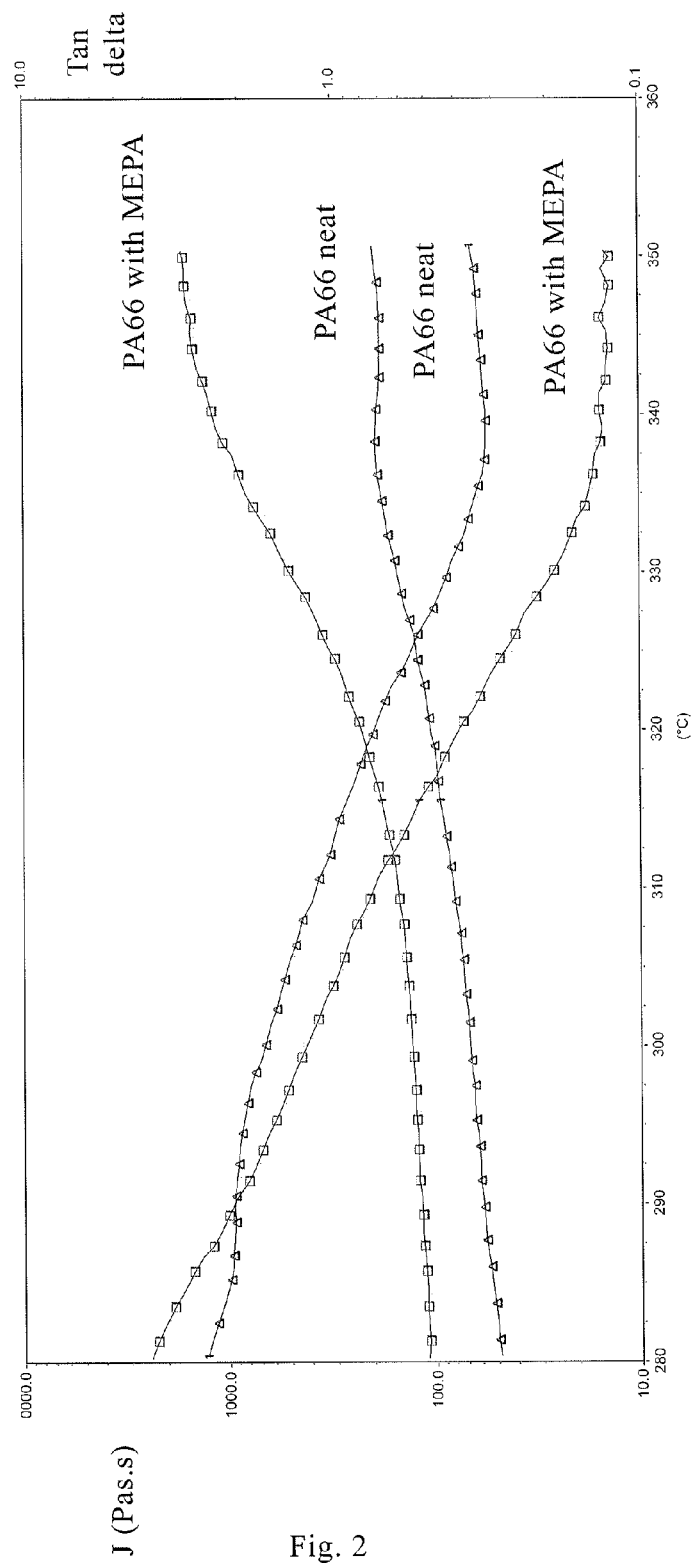
FIG. 2 depicts a viscosity/temperature scan of PA66 neat and end-capped with MEPA.

As seen from FIG. 2, the cross-linking is activated at about 310° C. This confirms that PA66 end-capped with MEPA may be processed without initiating cross-linking to any large extent. Further, the results confirm that polyamides end-capped with MEPA may be cross-linked without significant thermo degradation.

Figure 3:
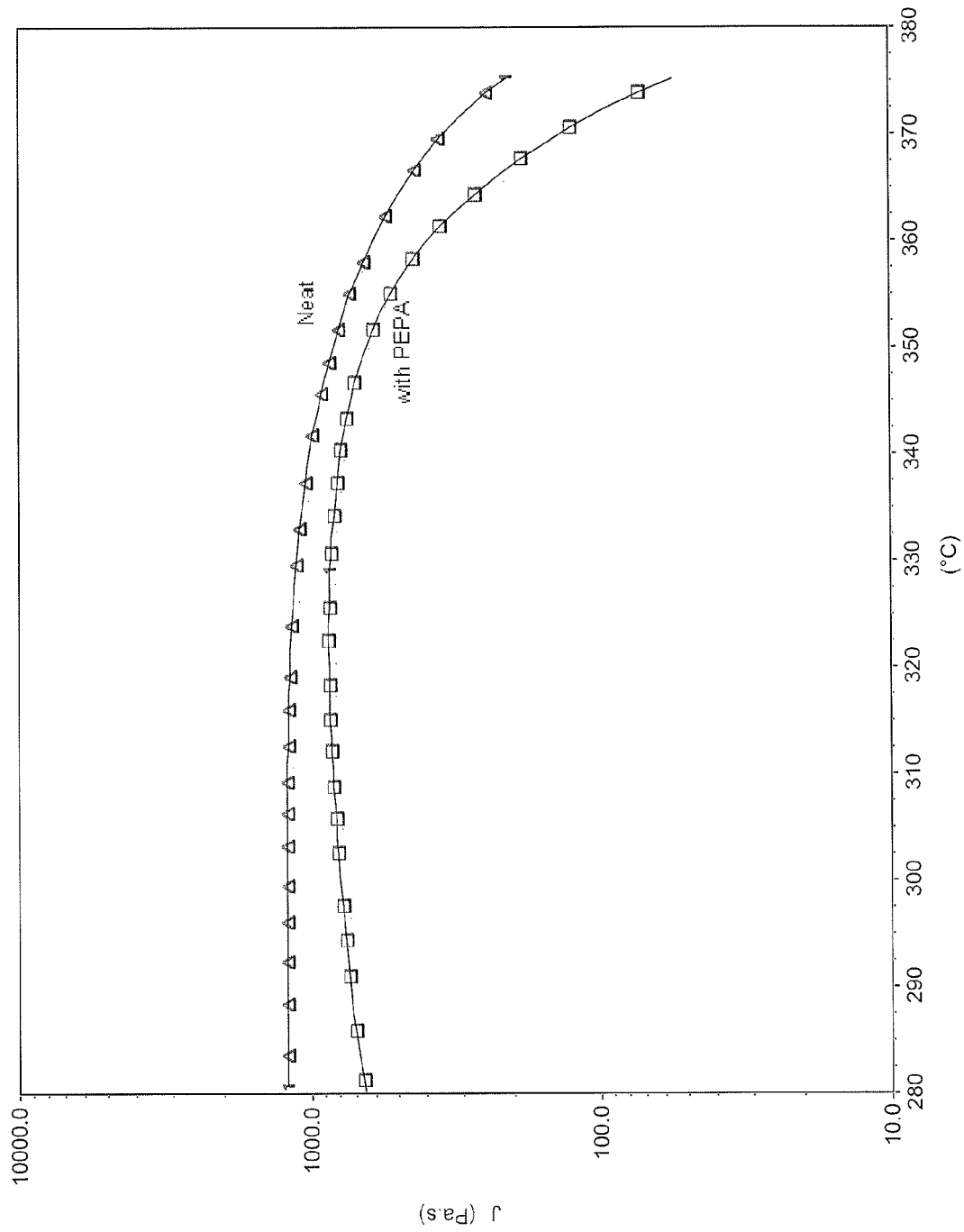
FIG. 3 depicts a viscosity/temperature scan of PA66 neat and end-capped with PEPA

From FIG. 3, depicting the melt viscosity as a function of temperature for PA66 end-capped with PEPA and neat PA66, respectively, it may be concluded that cross-linking of PA66 end-capped with PEPA is activated at 350° C., but no build up of viscosity is seen as the polymer is degraded at such a high temperature.

From FIGS. 2 and 3 it may thus be concluded that PA66 end-capped with MEPA, in contrast to PA66 end-capped with PEPA, may be cross-linked without any significant thermo degradation.

Attempts to end-cap PA66 with EPA by melt mixing were unsuccessful as the melted PA66 got very viscous upon addition of EPA, indicating that cross-linking is initiated already during processing.

Hexamethylene diamine endcapped with MEPA (HD-MEPA; 2,2'-(hexane-1,6-diyl)bis(5-(prop-1-yn-1-yl)isoindoline-1,3-dione))

281 g of hexamethylene diamine was added to 4200 ml of acetic acid. The mixture was heated to 50° C., whereupon 900 g of MEPA was added. The resulting mixture was heated to 67° C. and stirred during 120 min. Then the mixture was heated and refluxed during 17 hours, whereupon the mixture was cooled to 30° C. during 120 min. The resulting suspension was filtered and the solid was washed twice with 500 ml of acetic acid. The product was dried in vacuum at 75° C. over night to give 1038 g (95% yield) of a HD-MEPA as a pale beige solid product.

Melting Point of HD-MEPA 115-116° C. (as determined with DSC)

H-NMR of HD-MEPA $^1$H NMR (400 MHz, DMSO-d6): δ 7.81-7.76 (4H, m), 7.73 (2H, bs), 3.52 (4H, t, J=6.8), 2.12 (6H, s), 1.57-1.53 (4H, m), 1.29-1.25 (4H, m).

Preparation of PA66/MEPA/HD-MEPA Compound

PA66/MEPA/HD-MEPA compound (1.0 weight % MEPA, 10.0 weight % HD-MEPA) was prepared using a co-rotating twin-screw extruder (Coperion, ZSK26) with the screw diameter D=26 mm, screw length L=40D and a standard screw configuration containing conveying, kneading and mixing elements. The barrel temperature was set at 270° C. The base polymer, (PA66), and MEPA were fed at 8900 g/hour and 100 g/hour, respectively, to the main intake using two gravimetric feeders (Brabender Technologie). The HD-MEPA was fed at 1000 g/h to the extruder using a gravimetric feeder (Brabender Technologie) and a side-feeder connected in series, which were located at 26 D downstream from the main intake. Subsequent to exit from the extruder die, the compound strand was cooled and dried using a water batch (L=4 m) and an air-knife. Finally the strand was fed into a pelletizer, yielding the compound in granular form.

Thermal and Rheological Characterization of PA66/MEPA/HD-MEPA Compound

Figure 4:
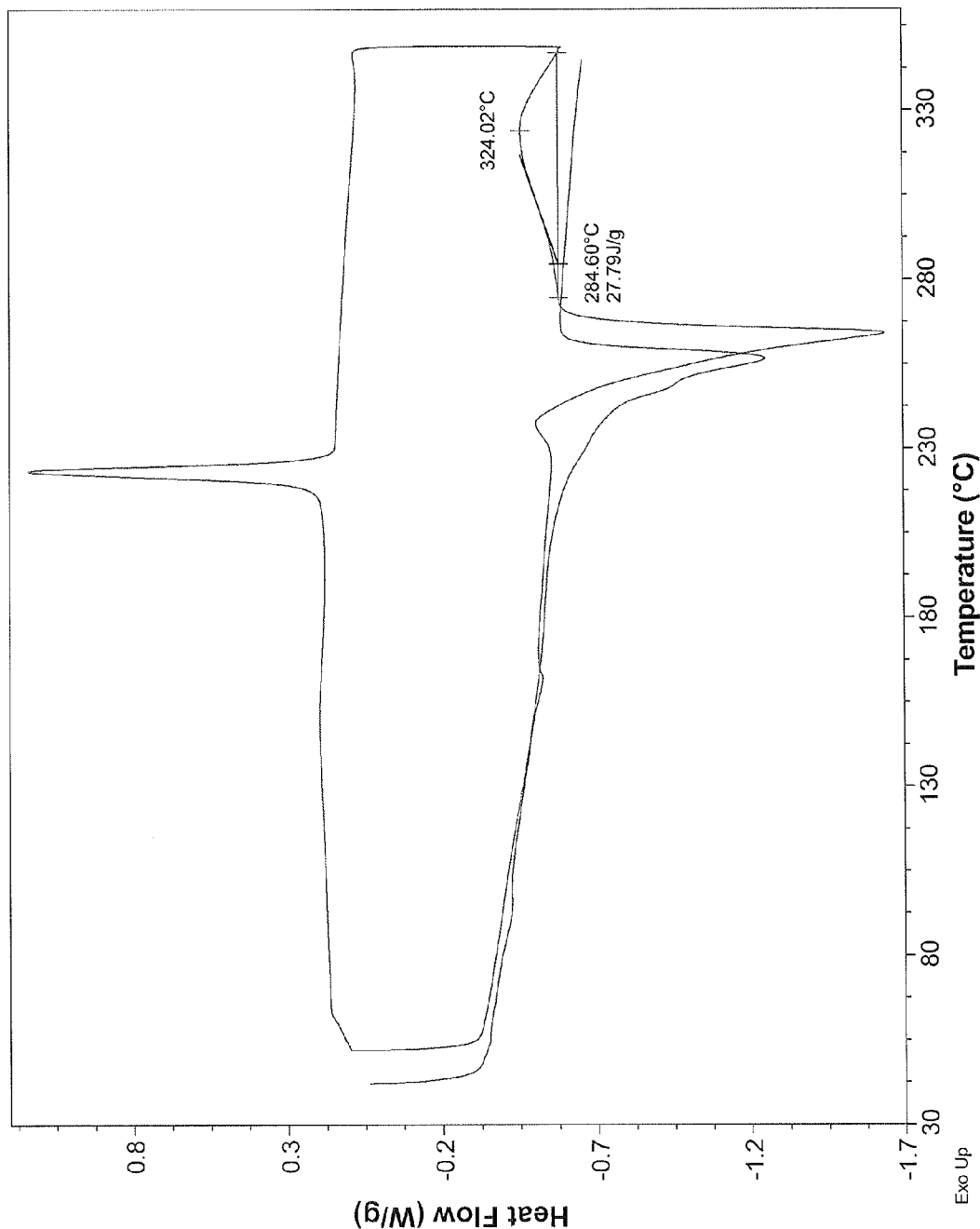
FIG. 4 depicts a thermogram of PA66-MEPA-HDMEPA compound as measured by differential scanning calorimetry (DSC).

PA66/MEPA/HD-MEPA compound was analyzed by differential scanning calorimetry (DSC), where the material was first heated from room temperature to 350° C. with a heating rate of 10° C./min, followed by cooling to 50° C. at 5° C./min and finally heated again to 350° C. at ° C./min. FIG. 4 shows a typical thermogram of the PA66/MEPA/HD-MEPA compound. The onset temperature for the curing exotherm was determined to 285° C., and the cure maximum to 324° C.

Figure 5:
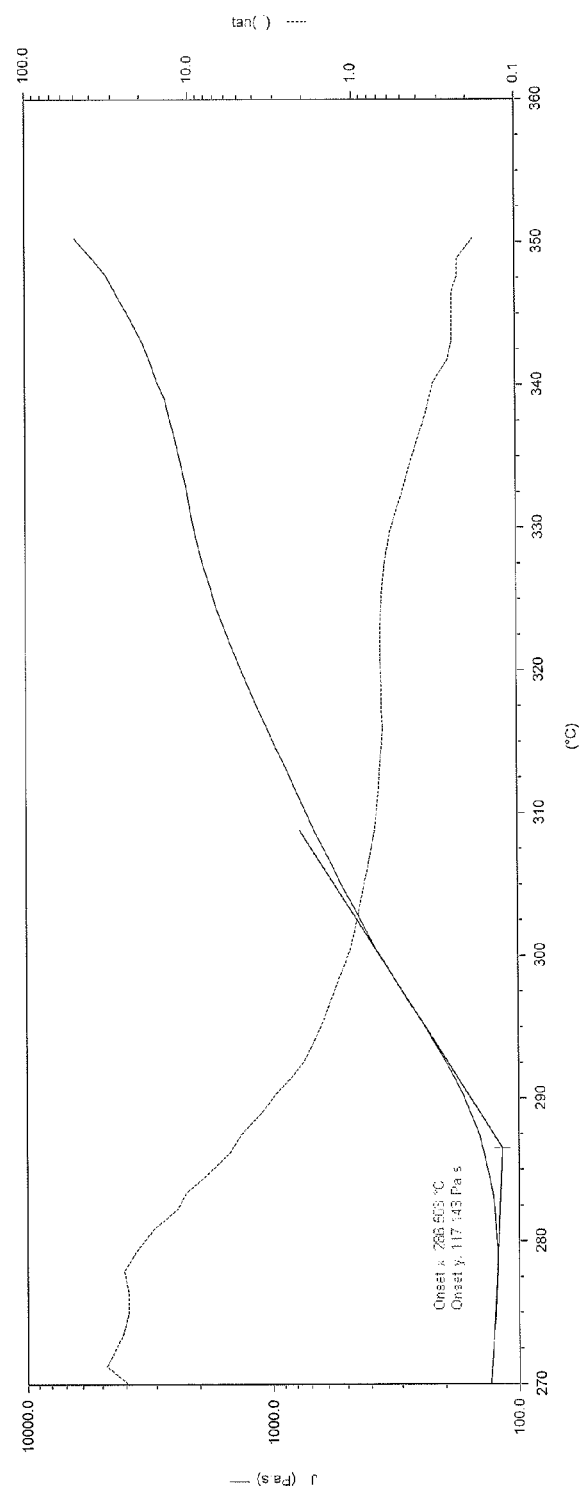
FIG. 5 depicts the complex melt viscosity and tan δ as functions of temperature of PA66-MEPA-HDMEPA compound as measured by parallel plate rheometry.

Complex melt viscosity of the PA66/MEPA/HD-MEPA compound was measured by strain oscillation using a parallel plate-plate rheometer (TA Instruments, ARES-G2). The plate distance was 1 mm, oscillating frequency 1 rad/s, strain 10% and the melt temperature was ramped from 270° C. to 350° C. at 5° C./min. Complex viscosity and tan δ as function of temperature can be seen in FIG. 5. The cure onset temperature was determined to 287° C.

The invention claimed is:

1. The compound 5-(prop-1-yn-1-yl)isobenzofuran-1,3-dione.

2. A compound comprising at least one residue according to formula (IV),

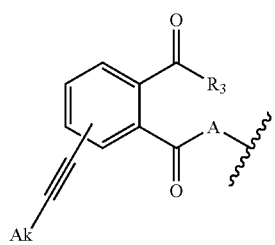

(IV)

wherein the waved line indicates the point of attachment to the rest of the compound;

"Ak" is a C1-10 alkyl or C0-1 alkylene cyclohexyl;

"A" is "O" (oxygen); and

R3 is OH, OC1-C8 alkyl, NH2, NHC1-8 alkyl, N(C1-8 alkyl)$_2$, wherein said alkyl may be the same or different, OC0-1 alkylenephenyl, NHC0-1 alkylenephenyl,

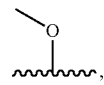

wherein the waved line indicates the point of attachment to the rest of the compound, or

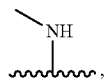

wherein the waved line indicates the point of attachment to the rest of the compound; and wherein said compound is an oligo- or polyester.

3. A compound according to formula XX

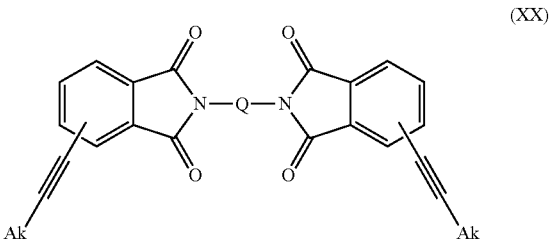

(XX)

wherein "Ak" is C1-10 alkyl or C0-1 alkylene cyclohexyl; and

Q is selected from the group consisting of C2-12 alkylene, phenylene, C1-4 alkylene-phenylene-C1-4 alkylene, or C0-4 alkylene-cyclohexandiyl-C0-4 alkylene.

4. The compound according to claim 3, wherein "Ak" is methyl, ethyl, propyl, iso-propyl, n-butyl, tert-butyl, n-pentyl, or neopentyl, and "Q" is tetramethylene, hexamethylene, or phenylene.

5. The compound according to claim 3, wherein said compound is 2,2'-(hexane-1,6-diyl)bis(5-(prop-1-yn-1-yl)isoindoline-1,3-dione).

6. A composition comprising:

an oligo- or polyamide, said oligo- or polyamide comprising:

a) a residue according to formula (III) or (IV),

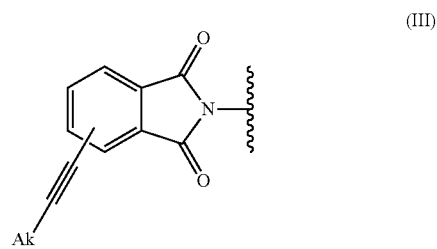

(III)

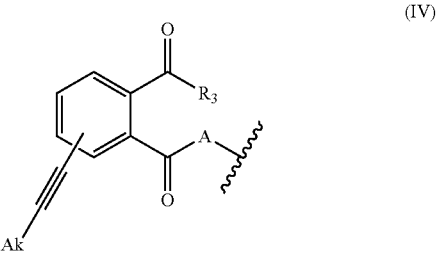

(IV)

wherein the waved line indicates the point of attachment to the rest of the oligo- or polyamide;

"Ak" is a C1-10 alkyl or C0-1 alkylene cyclohexyl;
"A" is NH;
R3 is OH, OC1-08 alkyl, NH2, NHC1-8 alkyl, N(C1-8 alkyl)$_2$, wherein said alkyl may be the same or different, OC0-1 alkylenephenyl, NHC$_{0-1}$ alkylenephenyl, or

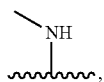

wherein the waved line indicates the point of attachment to the rest of the oligo- or polyamide; and
   b) at least 10 residues of a monomer selected from the group consisting of hexamethylene diamine, pentamethylene diamine, 2,2,4-trimethyl-hexamethylene diamine, 2,4,4-trimethyl-hexamethylene diamine, 1,4-diaminobutane, 1,2-diaminobenzene, 1,3-diaminobenzene, and 1,4-diaminobenzene, and at least 10 residues of a monomer selected from the group consisting of oxalic acid, maloic acid, adipic acid, sebacic acid, isophthalic acid, terephthalic acid, and 2,5-furandicarboxylic acid; or
at least 10 residues of a monomer selected from the group consisting of caprolactame, 11-aminoundecanoic acid, 12-aminodecanoic acid, and aminocaproic acid;
said oligo- or polyamide being present in an amount corresponding to at least 10 wt %; and
a compound according to formula XX

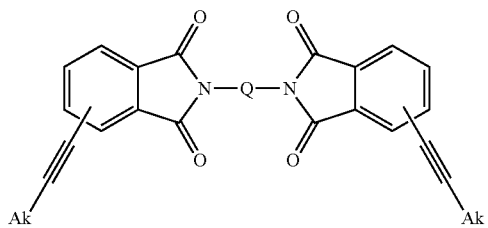
(XX)

wherein "Ak" is C1-10 alkyl or C0-1 alkylene cyclohexyl; and

Q is selected from the group consisting of C2-12 alkylene, phenylene, C1-4 alkylene-phenylene-C1-4 alkylene, or C0-4 alkylene-cyclohexandiyl-C0-4 alkylene;
said compound according to formula XX being present in an amount corresponding to at least 1 wt %;
a compound according to formula (I) or (II)

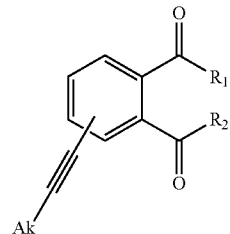
(I)

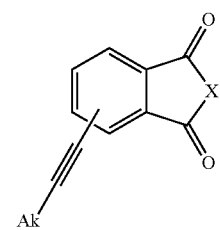
(II)

wherein
R1 and R2 are independently selected from the group consisting of OH, halo, OC1-08 alkyl, NH2, NHC1-8 alkyl, N(C1-8 alkyl)$_2$, wherein said alkyl may be the same or different, OC(O)C1-8 alkyl, OC0-1 alkylenephenyl, and NHC0-1 alkylenephenyl;
"Ak" is a C1-10 alkyl or C0-1 alkylene cyclohexyl; and
"X" is selected from the group consisting of "O" (oxygen), NH, NC1 alkylenephenyl, and NC1-8 alkyl; or "X" is Nphenyl; and/or
an additional polymer, and/or at least one filler, reinforcement, pigment, external flame retardant, stabilizer, and/or plasticizer.

* * * * *